United States Patent [19]

Richter

[11] 4,026,943

[45] May 31, 1977

[54] NOVEL PROCESS

[75] Inventor: Reinhard H. Richter, North Haven, Conn.

[73] Assignee: The Upjohn Company, Kalamazoo, Mich.

[22] Filed: Sept. 20, 1976

[21] Appl. No.: 724,584

[52] U.S. Cl. .............................................. 260/563 B
[51] Int. Cl.$^2$ ......................................... C07C 87/32
[58] Field of Search ................................ 260/563 B

[56] References Cited

UNITED STATES PATENTS

| 3,153,088 | 10/1964 | Arthur | 260/563 B |
| 3,155,724 | 11/1964 | Arthur | 260/563 B |
| 3,347,917 | 10/1967 | Arthur | 260/563 B |
| 3,384,661 | 5/1968 | Arthur | 260/563 B |
| 3,391,188 | 7/1968 | Arthur | 260/563 B |
| 3,393,236 | 7/1968 | Kuszewski | 260/563 B |

FOREIGN PATENTS OR APPLICATIONS

| 47-38438 | 9/1972 | Japan | 260/563 B |
| 46-15294 | 4/1971 | Japan | 260/563 B |

Primary Examiner—Paul F. Shaver
Attorney, Agent, or Firm—Denis A. Firth; John Kekich

[57] ABSTRACT

The trans-trans-isomer content of a mixture of stereoisomers of di-(p-aminocyclohexyl)methane is enriched by treating the latter mixture, optionally in solution in an organic solvent, with the trans,trans-isomer of a bisbenzaldimine of di-(p-aminocyclohexyl)methane.

8 Claims, No Drawings

NOVEL PROCESS

BACKGROUND OF THE INVENTION

1. Field of the Invention

This invention relates to a process for changing the stereoisomeric content of cycloaliphatic diamines and is more particularly concerned with increasing the proportion of trans,trans-stereoisomer in a mixture of stereoisomers of di-(p-aminocyclohexyl)methane.

2. Description of the Prior Art

Di-(p-aminocyclohexyl)methane is generally prepared by the catalytic hydrogenation of di-(p-aminophenyl)methane; see, for example, U.S. Pat. Nos. 2,494,563; 2,606,924; 2,606,928; 3,591,635 and 3,856,862. The products so obtained are found to be mixtures of the various possible stereoisomers, namely, the cis,cis-, cis,trans- and trans,trans-isomers.

For many purposes it is desirable to employ the substantially pure trans,trans-isomer. For example, polyamides derived from the latter isomer and dibasic aliphatic and aromatic carboxylic acids produce synthetic fibers having highly desirable properties; see, for example, Tedder et al., Basic Organic Chemistry, Part 5, pp. 283-4, John Wiley and Sons, London, 1975. Various methods are known for separating the more desirable trans,trans-isomer from the other isomers; see, for example, French specification No. 2,012,261 (Chem. Abstracts, 73, 130691, 1970) and German OLS 1,810,924 (Chem. Abstracts, 73, 66133, 1970). It is obviously desirable to seek to increase the trans,trans-isomer content in a mixture of this and the other stereoisomers before subjecting said mixture to separation for the isolation of the trans,trans-isomer. The process of this invention is directed to this object, namely, to a method of enriching the trans,trans-isomer in a mixture of the stereoisomers of di-(p-aminocyclohexyl)methane.

SUMMARY OF THE INVENTION

This invention comprises a process for enriching the trans,trans-isomer content of a mixture of stereoisomers of di-(p-aminocyclohexyl)methane which process comprises maintaining a mixture of (i) said mixture of stereoisomers and (ii) the trans,trans-isomer of a bis-benzaldimine of di-(p-aminocyclohexyl)methane of the formula:

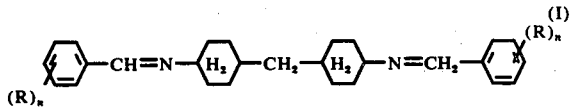

wherein R is an inert substituent and $n$ is an integer from 0 to 3, at a temperature in the range of about 15° C to about 60° C for a time sufficient to effect an increase in the trans,trans-isomer content of said diamine; and isolating from the product said diamine enriched in trans,trans-isomer content.

The term "inert substituent", as used herein in the specification and claims, means a substituent which does not enter into reaction with the other components of the reaction mixture employed in the process of the invention or in any other way interfere with the desired course of the reaction. Examples of such substituents are lower-alkyl, i.e., alkyl from 1 to 6 carbon atoms, inclusive, such as methyl, ethyl, propyl, butyl, pentyl, hexyl and isomeric forms thereof; lower-alkoxy, i.e. alkoxy from 1 to 6 carbon atoms, inclusive, such as methoxy, ethoxy, propoxy, butoxy, pentyloxy, hexyloxy and isomeric forms thereof; dialkylamino, wherein each alkyl is lower-alkyl as above defined, such as dimethylamino, diethylamino, dihexylamino, N-methyl-N-butylamino, and the like; halogen, i.e., chlorine, fluorine, bromine, iodine; and lower-alkyl-mercapto, i.e., alkylmercapto from 1 to 6 carbon atoms, inclusive, such as methylmercapto, ethylmercapto, propylmercapto, butylmercapto, pentylmercapto, hexylmercapto, and isomeric forms thereof.

DETAILED DESCRIPTION OF THE INVENTION

The process of the invention can be employed to convert the cis,cis-stereoisomer of di-(p-aminocyclohexyl)methane into a mixture of cis,cis-, cis,trans- and trans,trans-isomers or to enrich the trans,trans-isomer content of a mixture of said stereoisomers wherein the cis,cis-isomer of the starting mixture is at least about 40 percent by weight. Illustrative of the latter mixtures are those obtained by the catalytic hydrogenation of di-(p-aminophenyl)methane using the procedures cited hereinabove.

In carrying out the process of the invention the diamine II which is to be isomerized is brought together with the trans,trans-isomer of the bis-benzaldimine (I). Preferably, but not necessarily, the two components are brought together in the presence of an inert organic solvent in which the materials are mutually soluble. By "inert organic solvent" is meant an organic solvent which does not react with either the diamine (II) or the bis-benzaldimine (I) or interfere in any other way with the desired course of the reaction. Illustrative of inert organic solvents are benzene, toluene, xylene, chlorobenzene, chloroform, methylene chloride, carbon tetrachloride, diethyl ether, tetrahydrofuran, dimethylsulfoxide, ethyl acetate, dimethylformamide, dimethylacetamide, hexamethylphosphoramide, and the like.

The diamine (II) and the bis-benzaldimine (I) are employed in molar proportions ranging from about 1:1 to about 4:1 and preferably are employed in approximately equimolar proportions. The mixture of the two components (in the inert organic solvent if one is employed) is allowed to stand, advantageously with stirring, at ambient temperature, i.e., from about 15° C to about 30° C but elevated temperatures up to about 60° C can be employed if desired. The progress of the isomerization can be followed by taking aliquots of the solution and determining the stereoisomeric content thereof by $^{13}C$ nuclear magnetic resonance spectroscopy. The degree of isomerization which takes place depends in part on the overall proportion of cis to trans isomers in the starting mixture of stereoisomers of the diamine (II) and, in part, on the molar proportion of diamine (II) to benzaldimine (I) employed in the process of the invention. The isomerization will proceed until an equilibrium point is reached, the proportion of cis to trans isomers at the equilibrium point in any given instance depending upon the above factors. When the equilibrium point is reached in any given instance, no further isomerization will take place even at temperatures above those discussed above. When the above equilibrium point has been reached, the diamine (II) with the changed isomer content is separated from the bis-benzaldimine (I) using routine procedures; for example, the diamine (II) is extracted from the final solution or mixture using an aqueous mineral acid such as hydrochloric acid, the acid extract is neutralized and the precipitated diamine (II) is isolated by filtration, solvent extraction and the like. The bis-benzaldimine (I) is also recovered readily by evaporation of the inert organic solvent (if any) after the diamine (II) has been extracted as described above. It is found that the recovered bis-benzaldimine (I) is now a mixture of cis,cis-, cis,trans- and trans,trans-isomers, the overall proportion of cis-isomer which has been produced in the bis-benzaldimine (I) being substantially equal to the overall reduction in cis-isomer which has been produced in the diamine (II).

Accordingly, it is believed that what occurs in the process of the invention is an exchange reaction in which a portion of the cis,cis-isomer or cis-trans-isomer in the starting diamine (II) replaces the trans,trans-isomer of the diamine residue in the bis-benzaldimine (I). It is to be understood that the above is offered for purposes of explanation only and is not to be interpreted as limiting the scope of the present invention in any way.

The recovered bis-benzaldimine (I), which now contains a proportion of cis,cis- and cis-trans-isomers as well as the starting trans,trans-isomer, can be readily isomerized to obtain substantially pure trans,trans-isomer by the process which will be described hereafter. The trans,trans-isomer so recovered is then employed in a subsequent run of the process of the invention.

While the process of the invention has been described above as being carried out in solution in an inert organic solvent, it is found in certain instances that the starting diamine (I) and the bis-benzaldimine (II) are sufficiently low in melting point that they can be admixed in the fluid state and maintained in the fluid state without the need to employ a solvent. This is particularly true in the case where the bis-benzaldimine (I) is derived from benzaldehyde itself, i.e. $n$ represents 0 in the formula (I) of the bis-benzaldimine. Accordingly, in such cases the process of the invention can be carried out in the absence of an inert organic solvent.

The trans,trans-isomer of the bis-benzaldimine (I) which is employed in the process of the invention is obtained by a process which is described and exemplified very fully in my companion case Ser. No. 724585 filed on an even data herewith. Thus, a stereoisomeric mixture of di-(p-aminocyclohexyl)methane containing cis,cis-, cis-trans- and trans,trans-isomers in any proportion is converted to the corresponding bis-benzaldimine by reaction with the appropriate benzaldehyde

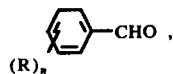

wherein R and $n$ have the significance above defined, under conditions well-known in the art for the formation of Schiff's bases; see, for example, Houben-Weyl-Muller, Methoden der organische Chemie, 7/1, 453, 1954. The reaction is represented by the following equation:

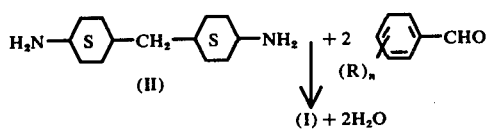

wherein R and $n$ have the significance hereinbefore defined. Each of the stereoisomers present in the starting diamine gives rise to the corresponding stereoisomer of the bis-benzaldimine (I).

Advantageously, the above reaction is carried out by bringing the diamine and the benzaldehyde together, optionally in the presence of an inert organic solvent. The reaction is generally exothermic, proceeds very readily, and does not require the application of any external heat. Indeed, cooling of the reaction mixture may be necessary in certain cases to control the reaction.

The diamine and the benzaldehyde are employed in substantially stoichiometric proportions, i.e., 2 moles of benzaldehyde per mole of diamine but a slight excess of benzaldehyde can be employed if desired. The water which is eliminated in the condensation is removed by distillation at the end of the reaction or while the reaction is in progress. The use of a solvent such as benzene in the reaction facilitates the removal of the water of condensation as an azeotrope either during the reaction or after completion thereof.

The bis-benzaldimine (I) so formed is generally a solid which remains as the residue after the removal of water and solvent, if one has been used in the condensation. The bis-benzaldimine can be purified by crystallization and like procedures, if desired, prior to the isomerization step which follows.

Illustrative of the benzaldehydes which can be used in the above condensation are benzaldehyde, anisaldehyde, m-methoxybenzaldehyde, p-ethoxybenzaldehyde, p-butoxybenzaldehyde, p-hexyloxybenzaldehyde, 3,4-dimethoxybenzaldehyde, 3,4,5-trimethoxybenzaldehyde, m-tolualdehyde, p-ethylbenzaldehyde, m-butylbenzaldehyde, p-hexylbenzaldehyde, 3,4,5-trimethylbenzaldehyde, p-methylmercaptobenzaldehyde, p-butylmercaptobenzaldehyde, p-dimethylaminobenzaldehyde, p-diethylaminobenzaldehyde, 3-methyl-4-dimethylaminobenzaldehyde, p-chlorobenzaldehyde, m-fluorobenzaldehyde, and the like.

The mixture of stereoisomers of bis-benzaldimine prepared as described above is then dissolved or suspended in an inert organic solvent and subjected to the action of a base at ambient temperatures, i.e., temperatures in the range of about 15° C to about 30° C or at elevated temperatures up to about 60° C or even higher if desired. Illustrative of bases which are employed are alkali metal hydroxides such as potassium hydroxide, lithium hydroxide, cesium hydroxide, and the like; alkali metal alkoxides such as potassium, lithium and cesium methoxides, ethoxides, t-butoxides and the like. Advantageously, the amount of said base employed is within the range of about 15 to about 100 mole percent based on bis-benzaldimine and is preferably within the range of about 30 to about 50 mole percent based on bis-benzaldimine.

Illustrative of the organic solvents which are employed in the above isomerization stage of the reaction are ethers such as dimethoxyethane, tetrahydrofuran, the cyclic polyethylene ether known as 18-crown-6-ether, dimethylsulfoxide, dimethylformamide, hexamethylphosphoramide, and the like.

The treatment of the solution of the bis-benzaldimine with the base is continued until the isomerization of the cis,cis- and cis,trans-isomers of the bis-benzaldimine to the corresponding trans,trans-isomer is adjudged to be substantially complete. The latter point can be determined by subjecting aliquots of the reaction mixture to analytical techniques such as $^{13}$C nuclear magnetic resonance spectroscopy.

The bis-benzaldimine is substantially pure trans,trans form obtained as described above can be isolated from the reaction product by conventional procedures, for example, by neutralization of the base catalyst followed by removal of the solvent. The product so obtained can be purified, if desired, by recrystallization and the like procedures.

The process of the invention gives rise to a stereoisomeric mixture of di-(p-aminocyclohexyl)methanes which is rich in the trans,trans-isomer, the overall ratio of cis- to trans-isomers in the mixture produced by the process being of the order of 35:65 depending on the various factors discussed above. This mixture is useful for all purposes for which di-(p-aminocyclohexyl)methane is known to be useful but is especially useful as intermediate in the known processes for separation of trans,trans-isomers from the other isomers. The use of trans,trans-rich mixture produced by the process of the invention gives an increased overall yield of trans,trans-isomer in the separation of the isomers as compared with the starting mixture used in the process of the invention.

The following examples describe the manner and process of making and using the invention and set forth the best mode contemplated by the inventor of carrying out the invention but are not to be construed as limiting.

EXAMPLE 1

Preparation of the trans,trans-isomer of bis-benzaldimine of di-(p-aminocyclohexyl)methane.

A mixture of 21.0 g. (0.1 mole) of di-(p-aminocyclohexyl)methane [shown by $^{13}$C nuclear magnetic resonance (NMR) spectroscopy to contain an overall cis-trans-isomer ratio of 72:28] and 21.2 g. (0.2 mole) of benzaldehyde in 100 ml. of benzene was heated under reflux using a Dean-Stark apparatus until no more water was eliminated in the azeotrope. The resulting solution was evaporated to dryness to leave, as a solid residue, the bis-benzaldimine of di-(p-aminocyclohexyl)methane in the form of a mixture of the cis,-cis-, cis,trans- and trans,trans-isomers, the overall ratio of cis to trans being 72:28.

A mixture of 5 g. (0.013 mole) of the bis-benzaldimine prepared as described above, 10 ml. of dimethoxyethane, 0.2 g. of 18-crown-6 [cyclic poly(oxyethylene): Parish Chemical Company, Provo, Utah] and 1 g. (0.018 mole) of powdered potassium hydroxide was stirred for 24 hours at room temperature (circa 20° C). The resulting mixture was allowed to stand for a further 71 hours at the same temperature before evaporating the solvent and triturating the residue with water. The solid material was isolated by filtration, washed with water and dried at 70° C. There was thus obtained a quantitative yield of the bis-benzaldimine which was shown, by $^{13}$C NMR spectroscopy, to have a trans,-trans-isomer content of greater than 95 percent by weight.

EXAMPLE 2

A solution containing 1.93 g. (0.005 mole) of the trans,trans-benzaldimine prepared as described in Example 1 and 1.05 g. (0.005 mole) of di-(p-aminocyclohexyl)methane (containing an overall ratio of cis/-trans-isomers of 71:29) in 6 ml. of methylene chloride was maintained at room temperature (circa 20° C) for 24 hours. At the end of this time an aliquot of the solution was evaporated to dryness and submitted to $^{13}$C nuclear magnetic resonance spectroscopy. The latter showed that the overall cis/trans ratio in the diamine was 33:66 and that in the benzaldimine was 35/65. The remainder of the solution was maintained for a further 24 hours at room temperature. At the end of this time it was found by $^{13}$C nuclear magnetic resonance spectroscopy of an aliquot that no further change in the overall cis/trans ratios in the diamine or the benzaldimine had taken place. The bulk of the material, after removing the solvent, was vacuum distilled to recover the diamine having an enriched content of trans,trans-isomer.

I claim:

1. A process for enriching the trans,trans-isomer content of a mixture of stereoisomers of di-(p-aminocyclohexyl)methane which process comprises maintaining a mixture of (i) said mixture of stereoisomers and (ii) the trans,trans-isomer of a bis-benzaldimine of di-(p-aminocyclohexyl)methane of the formula:

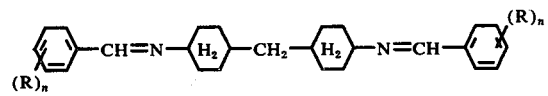

wherein R is an inert substituent and $n$ is an integer from 0 to 3, at a temperature within the range of about 15° C to about 60° C for a time sufficient to effect an increase in the trans,trans-isomer content of said diamine; and isolating from the product said diamine enriched in trans,trans-isomer content.

2. The process of claim 1 wherein the diamine and the benzaldimine are employed in approximately equimolar proportions.

3. The process of claim 1 wherein the reaction is carried out in the presence of an inert organic solvent.

4. The process of claim 3 wherein the organic solvent is methylene chloride.

5. The process of claim 1 wherein the benzaldimine has the formula:

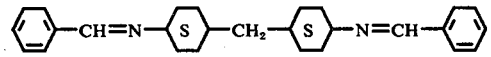

6. A process for enriching the trans,trans-isomer content of a mixture of stereoisomers of di-(p-aminocyclohexyl)methane which process comprises maintaining an inert organic solvent solution of said mixture of stereoisomers and the trans,trans-isomer of the bis-benzaldimine of di-(p-aminocyclohexyl)methane at a temperature of 15° C to 60° C until no further significant change in stereoisomer proportions occurs and thereafter isolating said diamine enriched in trans,trans-isomer content.

7. The process of claim 6 wherein said inert organic solvent is methylene chloride.

8. The process of claim 6 wherein the said diamine and said benzaldimine are employed in substantially equimolar proportions.

* * * * *